United States Patent [19]

Fiedler-Linnersund et al.

[11] 4,224,114
[45] Sep. 23, 1980

[54] METHOD AND APPARATUS FOR DETECTING ZINC ION ACTIVITY

[76] Inventors: Ulla M. Fiedler-Linnersund, c/o Analytical Chem. Univ. of Lund, P.O. Box 740, S-220 07 Lund, Sweden; Khan M. Bhatti, 4, Zakaria Lodge Abba Samar St., Ghari Khata Karachi, Pakistan; Gillis Johansson, c/o Anal. Chem. Univ. of Lund, P.O. Box 740, S-220 07 Lund, Sweden

[21] Appl. No.: 41,743

[22] Filed: May 24, 1979

[51] Int. Cl.$^3$ ............ G01N 27/30; G01N 27/46
[52] U.S. Cl. ............... 204/1 T; 204/195 M; 204/195 L
[58] Field of Search ............ 204/195 M, 195 L, 1 T

[56] References Cited

U.S. PATENT DOCUMENTS

| | | | |
|---|---|---|---|
| 3,429,785 | 2/1969 | Ross | 204/1 T |
| 3,438,886 | 4/1969 | Ross | 204/195 L |
| 3,445,365 | 5/1969 | Ross | 204/195 L |
| 3,483,112 | 12/1969 | Ross | 204/195 L |
| 3,497,424 | 2/1970 | Ross | 240/1 T |
| 3,671,413 | 6/1972 | Wise | 204/195 L |
| 3,691,047 | 9/1972 | Ross et al. | 204/195 M |
| 3,723,281 | 3/1973 | Wise | 204/195 L |
| 3,801,486 | 4/1974 | Wise | 204/195 L |
| 3,932,233 | 1/1976 | Ruzicka et al. | 204/195 M |

OTHER PUBLICATIONS

Lo Gorton et al., Analytica Chimica. ACTA vol. 90, pp. 233-236, (1977).
D. Ammann et al., Analytical Letters, vol. 5, No. 11, pp. 843-850, (1972).
A.G. Fogg et al., Analytical Letters, vol. 6, No. 12, pp. 1101-1106, (1973).

*Primary Examiner*—G. L. Kaplan
*Attorney, Agent, or Firm*—John B. Miller

[57] ABSTRACT

An electrode preferentially sensitive to the activity of zinc ions $Zn^{+2}$ in solution. A liquid organic phase containing an appropriate liquid ion exchanger and solvent is combined with means for containing the liquid organic phase as an interface between the organic phase and the solution. Electrical contact with the liquid organic phase at a fixed potential is provided. Zinc ion activity is measured using a standard calomel electrode as a reference, from which the zinc ion concentration is determined.

4 Claims, 3 Drawing Figures

METHOD AND APPARATUS FOR DETECTING ZINC ION ACTIVITY

BACKGROUND OF THE INVENTION

1. Field of Invention

This invention relates to electrochemical detection and measurement, and more particularly, to novel means for potentiometrically determining and measuring the presence of zinc ions in solution.

2. Prior Art Statement

Presently the zinc concentration of solutions can be determined spectroscopically and with voltammetric methods. These prior arts do not lend themselves to continuous, real-time monitoring and usually require sampling. Furthermore, these methods will measure either the total amount of zinc or the free and complex bound zinc in a sample. It is especially important in medicine and physiological research to measure ionic activity and this has not been possible with any method known before.

Electrochemical determination of ionic concentrations in solutions has been known for years. In a typical arrangement, a reference electrode and an ion-sensitive electrode are simultaneously immersed into the same body of solution creating an electrochemical cell across which an electric potential develops which is approximately proportional to the logarithm of the activity (or concentration) of the ion to which one of the electrodes is sensitive. A metering device measures the developed potential between the electrodes.

Many different techniques and structures have been developed to provide an ion-sensitive electrode. Of particular relevance to the present application are three patents which describe organic liquid ion exchangers: U.S. Pat. Nos. 3,429,785 issued Feb. 25, 1969 to James W. Ross; 3,445,365 issued May 20, 1969 to James W. Ross; and 3,438,886 issued Apr. 15, 1969 to James W. Ross. In U.S. Pat. No. 3,429,785, an electrode was provided for determining concentrations of ionic species in solution, and particularly for determining the concentration of polyvalent ionic species. The barrier means of this electrode comprises, in continuous phase, an ion-exchanger liquid. Disclosed are several examples of liquid cation exchangers, including normally liquid organophosphoric acids, such as di-2-ethylhexylphosphoric acid and either or both of the mono and di forms of n-butyl phosphoric acid and amyl phosphoric acid. Also disclosed is the use of an appropriate mediator liquid including alcohols with long aliphatic chains in excess of eight carbon atoms, such as octyl and dodecyl alcohols; ketones such as 2-pentanone; aromatic compounds such as nitrobenzene, orthodichlorobenzene, trialkylphosphonates; and mixtures containing phosphonates. These materials were found to produce a barrier means sensitive to polyvalent cations. In particular, an electrode formed of calcium di-2-ethylhexylphosphate as the ion-exchanger in a mediator of dioctyl phenyl phosphonate was found to be sensitive to calcium ions, $Ca^{+2}$.

In U.S. Pat. No. 3,445,365, which is a continuation-in-part of U.S. Pat. No. 3,429,785, Ross further discloses the use of means for restricting ion transfer across the barrier in the form of a diffusing membrane between the test solution and the ion-exchanger liquid. The membrane includes channels of finite size filled with liquid exchanger material so that the diffusion coefficient through the channels remains high but the average ion flux through the membrane is considerably less than would occur at a continuous exchanger—test solution interface of the same area as the membrane surface.

In U.S. Pat. No. 3,438,886, Ross discloses a structural variation of the above patents wherein the membrane is situated to serve as a wick which maintains a layer of the exchanger liquid between the reference solution and the solution in which the activity of ions is to be determined. The membrane is preferentially wetted by the exchanger liquid. The resulting electrode is preferentially selective for divalent over monovalent cations.

A large number of membrane materials have been examined during recent years. These have included different glasses for hydrogen-, sodium-, potassium-, and ammonium-ion electrodes, and inorganic salts for fluoride, chloride, bromide, iodide, cyanide, sulphide, copper, lead, cadmium and silver ion electrodes. Liquid state membranes have been employed for potassium, calcium, nitrate and perchlorate ions. The liquid can be soaked into a porous membrane made of filter paper or sintered glass so that a thin layer of organic solvent is formed between the sample solution and an inner solution in the electrode. The organic solvent should be immiscible with water. The liquid layer may also be immobilized by mixing with a polymer like polyvinylchloride or polyurethane. The liquid containing polymer can be cast or pressed into a membrane which is inserted between the sample solution and the inner solution. The liquid used in liquid state membrane electrodes is a mixture between a major component, considered to be the solvent, and a minor component, considered to be the ligand, which forms a complex with the ions to be measured.

Further developments in the liquid ion-exchanger field produced electrodes sensitive to other ionic species, such as: $ClO_4^-$, $Br^-$, $I^-$, $NO_3^-$, and $ClO_3^-$ in U.S. Pat. No. 3,483,112 issued Dec. 9, 1969; bicarbonate ion $HCO_3^-$ in U.S. Pat. No. 3,723,281 issued Mar. 27, 1973; chloride ion $Cl^-$ in U.S. Pat. No. 3,801,486 issued Apr. 2, 1974; nitrate ions $NO_3^-$ in U.S. Pat. No. 3,671,413 issued June 20, 1972.

In U.S. Pat. No. 3,497,424 issued Feb. 24, 1970 to James W. Ross, an electrode particularly sensitive to $Cu^{+2}$ ions in solution was disclosed and claimed. The ion-sensitive portion of the electrode is a body of an ion-exchanger liquid formed in a water-insoluble salt of S-alkyl thioglycolic acid dissolved in a water-immiscible solvent, such as a 50:50 mixture of decanol and o-dichlorobenzene.

In U.S. Pat. No. 3,691,047 issued Sept. 12, 1972 to James W. Ross and Martin S. Frant, a gel membrane sensitive to calcium ions $Ca^{+2}$ was disclosed and claimed. The membrane is formed of a gelled mixture wherein the solid phase is a substantially chemically inert polymeric matrix comprising cellulose triacetate and the liquid phase is an organic ion exchange material such as a salt of a phosphate ester dissolved in a substantially non-volatile solvent such as di-octylphenylphosphonate. Several calcium ion exchangers are disclosed in the patent.

In *Analytical Letters*, 5(11), 843–850 (1972), D. Ammann, E. Pretsch, and W. Simon published a paper entitled *A Calcium Ion-Selective Electrode Based On A Neutral Carrier* which describes a synthesized ligand in p-nitroethylbenzene as the membrane ion-sensitive component. The membrane is used in an electrode which measures $Ca^{+2}$ ion activity in the range of $10^{-1}$M to $10^{-5}$M in unbuffered systems with a selectivity of calcium over sodium and magnesium of 175 and 33,000 respectively.

All of the above references are distinguished from the present invention in that in none of these references is a barrier means (membrane) described in which the composition of the membrane renders the membrane primarily and preferentially selective to the presence of zinc ions, $Zn^{+2}$.

Other methods of measuring the concentration of zinc ions in solution have been reported. One indirect selective method using electrodes which measure Zn(II) as tetrathiocyanatozincate has been reported by A. G. Fogg, M. Duzinkewycz and A. S. Pathan in *Analytical Letters*, 6 (1973) 1101. A similar method measuring Zn(II) as tetrachlorozincate has been reported by R. W. Cattrall and C. P. Pui, *Analytical chim. Acta*, 87 (1976) 419. These indirect measurements of zinc (II) involve dilution of the original sample which may change the position of the equilibria between zinc-ions and different zinc containing complexes. In this respect the present invention, which measures zinc ion concentration directly, is distinguishable from the indirect methods.

A direct method of measuring zinc ion, $Zn^{+2}$, concentration was described by L. Gorton and V. Fiedler in *Anal. Chim. Acta*, 90 (1977) 233. Using a polymeric membrane electrode and mixing the sample with a calcium—precipitating buffer, the electrode could be made selective for zinc. In this method, dilution of the sample again introduces the possibility that the chemical equilibria between zinc-ions and zinc containing complexes is altered. The present invention overcomes this dilution limitation by providing an electrode applicable for the direct measurement of ionized zinc in a sample solution.

SUMMARY OF THE INVENTION

The present invention contemplates an electrode selective to the activity of zinc ions $Zn^{+2}$ in solution. One object of the invention is to provide a direct, continuous, real-time monitoring electrode for determining the activity of zinc ions $Zn^{+2}$ in solution. Another object of the invention is to provide an electrode primarily and preferentially selective to the activity of zinc ions $Zn^{+2}$ in solution.

The object of the invention are effected by providing an electrode wherein the ion-sensitive membrane portion is composed of a liquid organic phase containing an optimal liquid ion exchanger and an appropriate solvent (or mediator). Selectivity studies have shown that when the liquid ion-exchanger is di-2-ethylhexylphosphoric acid and the solvent is tri-2-ethylhexylphosphate, the liquid organic phase is primarily and preferentially selective to the activity of zinc ions $Zn^{+2}$. By adding polyvinylchloride to the liquid organic phase in appropriate ratios, the usual membrane electrode structure is obtained.

BRIEF DESCRIPTION OF THE DRAWINGS

For a more full understanding of the nature and objects of the invention reference should be made to the following detailed description taken in connection with the accompanying drawings wherein.

DETAILED DESCRIPTION OF THE INVENTION

Figure 1:
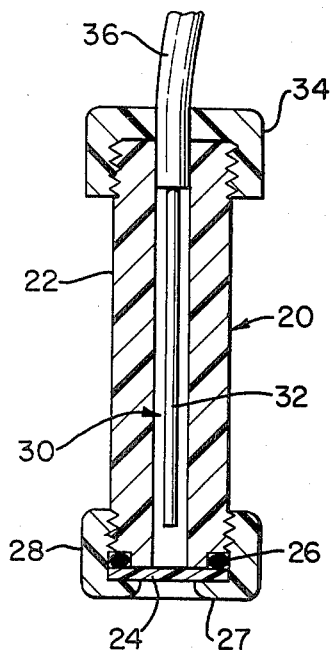
FIG. 1 shows a schematic side-elevational, cross-sectional simplified view of an electrode embodying the principles of the present invention.

Referring to the drawing there is shown in FIG. 1 electrode 20 embodying the principles of the present invention and comprising an elongated, hollow tubular container or stem 22 open at both ends. The stem typically is formed of a liquid-impervious, substantially rigid, electrically-insulating material, such as unplasticized polyvinylchloride, polytetrafluorethylene, glass or the like, substantially chemically inert to solutions being tested and with which the stem might be placed in contact.

On end of the stem 22 is capped or sealed with a barrier disc or membrane 24 which will be described in detail later herein. Membrane 24 can be quite thick, for example, $\frac{1}{4}''$, although thinner structures are preferred. Membrane 24 can be sealed across the one end of stem 22 with an appropriate sealing compound such as PVC, dissolved in tetrahydrofuran, but advantageously, as shown, is mounted on O-ring 26 disposed about the periphery of the opening in the stem, and held in a pressed fit against the O-ring by annular flange 27 of collar 28 threadedly mounted on the stem. When collar 28 is rotated in the proper direction, it advances axially, forcing membrane 24 in a tight fit against the O-ring, thus sealing the one end of stem 22. Both the O-ring and collar 28 are preferably made of a plastic material such as polyvinylchloride.

Disposed internally of stem 22 and in electrical and physical contact with the inner surface of membrane 24 is charge transfer means providing a fixed concentration of zinc in ionic form. This means is shown as a reference electrolyte 30. Immersed in electrolyte 30 is internal reference electrode 32, for example, the well-known Ag-AgCl element. This combination of electrolyte 30 and reference electrode 32 provides means for electrically contacting the internal face (i.e., the surface of the membrane contacting the electrolyte) as a substantially stable or fixed potential.

The other open end of stem 22 is fitted with annular cap 34 having an aperture in which is sealed the usual coaxial cable 36, the central conductor of which is connected to internal reference electrode 32 and the peripheral conductor of which is intended to provide electrostatic shielding.

The more important considerations in fabricating the electrode of FIG. 1 lie in the composition of membrane 24. The other elements and the shape and size of the electrode are not particularly critical and can be selected according to the anticipated use.

The membranes of the present invention are advantageously formed of a polymer, an organic solvent, and a liquid ion-exchanger, selected according to the desired response of the electrode. The mutual compatibility of the three membrane components is in this case a necessity. The membranes can also be formed by soaking the organic liquid phase composed of solvent and ion-exchanger into a porous material such as filter paper or sintered glass.

The following are examples of the preparation of the membranes used in the invention, and the responses of electrodes using such membranes. Where the response is noted as being Nernstian, it is intended to indicate that the ion-sensitive membrane responds substantially in accordance with the well-known Nernst Equation in a stable and reproducible manner.

EXAMPLE I 75 mg of the polymer polyvinychloride and 175 mg of the solvent tri-2-ethylhexylphosphate were dissolved in 3.0 ml of tetrahydrofuran. This solution was poured into a glass ring (diameter 24 mm, height 15 mm) resting on a glass plate and the tetrahydrofuran was allowed to evaporate slowly. In one day a polymeric PVC-membrane was formed (thickness 0.2 mm). Out of this master membrane an electrode membrane was cut and mounted in the electrode body to form a test electrode containing no liquid ion-exchanger.

This ion-exchanger-free electrode was used to measure activites of $Zn^{2+}$ in a number of aqueous $Zn(NO_3)_2$ solutions, buffered by 0.01 M HAc and 0.01 M KAc to pH=4.7. A saturated calomel electrode was used as a reference electrode as shown by electrode 42 in FIG. 2. Typically cell potentials are as follows for each solution of different concentration and corresponding activity, calculated in the usual way.

| Concentration of $Zn^{2+}$, M. | Activity of $Zn^{2+}$, M. | Reading in mV. |
|---|---|---|
| — (buffer) | — (buffer) | −47.1 |
| $1 \cdot 10^{-6.000}$ | $1 \cdot 10^{-6.175}$ | −46.5 |
| $1 \cdot 10^{-5.000}$ | $1 \cdot 10^{-5.175}$ | −46.0 |
| $1 \cdot 10^{-4.000}$ | $1 \cdot 10^{-4.177}$ | −42.0 |
| $1 \cdot 10^{-3.000}$ | $1 \cdot 10^{-3.195}$ | −16.5 |
| $1 \cdot 10^{-2.000}$ | $1 \cdot 10^{-2.303}$ | +27.3 |
| $1 \cdot 10^{-1.000}$ | $1 \cdot 10^{-1.548}$ | +64.2 |

To determine the effect of interfering cations on the electrode response, the electrode was tested in a number of aqueous 0.01 M solutions of alkali metal chlorides, alkaline earth metal chlorides and heavy metal nitrates. The following results were obtained, where selectivity coefficients were calculated according to the following equation:

$$\log K_{ZnM} = \frac{(E_{Mz+} - E_{Zn2+})2F}{2.303 \cdot R \cdot T} + \log a_{Zn2+} - \log a_{Mz+}^{2/z}$$

where Z is the valence of the cation.

| Cation (M) | Reading in Mv | $K_{ZnM}$ |
|---|---|---|
| $Li^+$ | +61.7 | $1 \cdot 10^{+0.28}$ |
| $Na^+$ | +10.5 | $1 \cdot 10^{-1.45}$ |
| $K^+$ | −22.2 | $1 \cdot 10^{-2.56}$ |
| $Rb^+$ | −35.8 | $1 \cdot 10^{-3.02}$ |
| $Cs^+$ | −35.8 | $1 \cdot 10^{-3.02}$ |
| $Mg^{2+}$ | −53.1 | $1 \cdot 10^{-4.27}$ |
| $Ca^{2+}$ | −10.5 | $1 \cdot 10^{-2.83}$ |
| $Sr^{2+}$ | −65.8 | $1 \cdot 10^{-4.70}$ |
| $Ba^{2-}$ | −64.0 | $1 \cdot 10^{-4.64}$ |
| $Cu^{2+}$ | +16.9 | $1 \cdot 10^{-1.91}$ |
| $Zn^{2+}$ | +73.3 | $1 \cdot 00$ |
| $Cd^{2+}$ | +10.4 | $1 \cdot 10^{-2.13}$ |
| $Pb^{2+}$ | +34.2 | $1 \cdot 10^{-1.32}$ |

EXAMPLE II

The zinc salt of di-2-ethylhexylphosphoric acid was prepared by equilibrating 100 ml of a methanolic solution containing 1.0 mmol of the acid ion-exchanger with the stoichiometric amount (0.5 mmol) of an aqueous solution of zinc nitrate (50 ml 0.010 M Zn $(NO_3)_2$) for about 3 hours. The white precipitate obtained was filtered, washed and dried.

15 mg of the zinc salt ion-exchanger was mixed with 160 mg of the solvent tri-2-ethylhexylphosphate and 75 mg of the polymer polyvinylchloride. The mixture was dissolved in 3.0 ml of tetrahydrofuran and a polymeric membrane was prepared as described in example I. An electrode membrane was cut and mounted in the electrode body to form an electrode containing an ion-exchanger.

Figure 2:
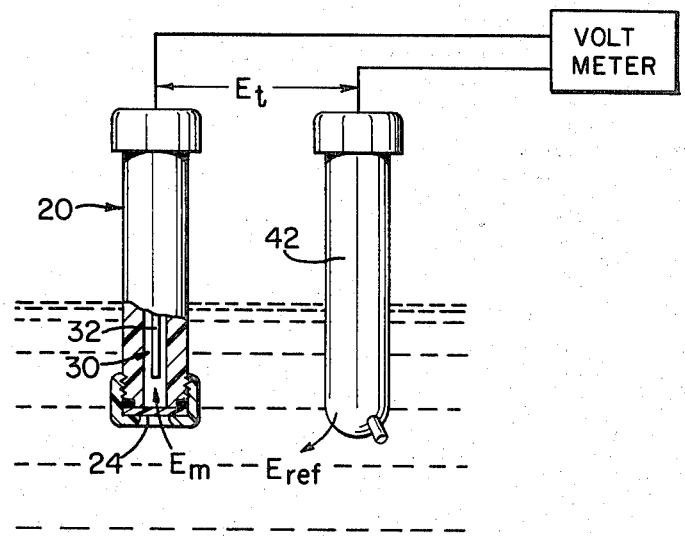
FIG. 2 is a schematic, side-elevational view, partly in cross section of a cell employing te electrode of FIG. 1 for the detection of zinc $Zn^{+2}$ ions.

This electrode was used to measure activities of $Zn^{2+}$ in a number of aqueous $Zn(NO_3)_2$ solutions, buffered by 0.01 M HAc and 0.01 M KAc to pH=4.7, with a system as shown in FIG. 2.

Typically cell potentials (with the saturated calomel electrode as reference electrode) are as follows for each solution of different concentration and corresponding activity, calculated in the usual way. The potential changes are small within several months for an electrode which is stored in a dry condition between measurements.

| Concentration of $Zn^{2+}$, M. | Activity of $Zn^{2+}$, M. | Reading in mV. |
|---|---|---|
| —(buffer) | —(buffer) | −49.6 |
| $1 \cdot 10^{-6.000}$ | $1 \cdot 10^{-6.175}$ | −49.0 |
| $1 \cdot 10^{-5.000}$ | $1 \cdot 10^{-5.175}$ | −47.5 |
| $1 \cdot 10^{-4.000}$ | $1 \cdot 10^{-4.177}$ | −34.2 |
| $1 \cdot 10^{-3.000}$ | $1 \cdot 10^{-3.195}$ | + 8.9 |
| $1 \cdot 10^{-2.000}$ | $1 \cdot 10^{-2.303}$ | +47.9 |
| $1 \cdot 10^{-1.000}$ | $1 \cdot 10^{-1.548}$ | +81.0 |

Figure 3:
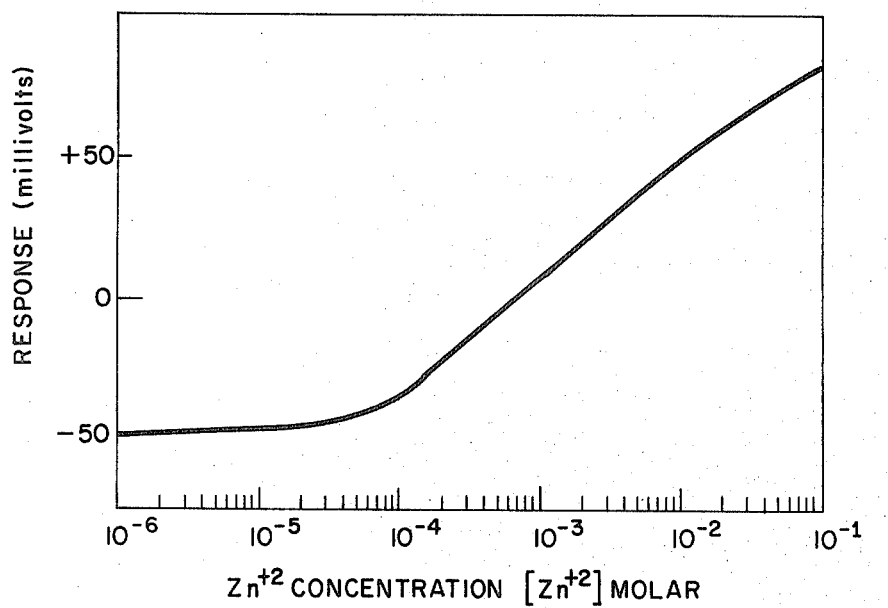
FIG. 3 is a semi-logarithmic graph showing the response of the cell of FIG. 2 for zinc ion measurements to solutions of different zinc ion activities.

These results are graphically displayed in FIG. 3.

To determine the effect of interfering cations on the electrode response, the electrode was tested in a number of aqueous 0.10 M solutions of alkali metal chlorides, alkaline earth metal chlorides and heavy metal nitrates. The following results were obtained, where selectivity coefficients were calculated according to equation (7):

| Cation | Reading in mV | $K_{ZnM}$ |
|---|---|---|
| $Li^+$ | +42.3 | $1 \cdot 10^{-0.32}$ |
| $Na^+$ | − 5.5 | $1 \cdot 10^{-1.94}$ |
| $K^+$ | −36.4 | $1 \cdot 10^{-2.99}$ |
| $Rb^+$ | −36.4 | $1 \cdot 10^{-2.99}$ |
| $Cs^+$ | −36.5 | $1 \cdot 10^{-2.99}$ |
| $Mg^{2+}$ | −33.3 | $1 \cdot 10^{3.55}$ |
| $Ca^{2+}$ | +16.3 | $1 \cdot 10^{-1.88}$ |
| $Sr^{2+}$ | −33.6 | $1 \cdot 10^{-3.56}$ |
| $Ba^{2+}$ | −39.7 | $1 \cdot 10^{-3.77}$ |
| $Cu^{2+}$ | +16.0 | $1 \cdot 10^{-1.89}$ |
| $Zn^{2+}$ | +71.8 | $1 \cdot 00$ |
| $Cd^{2+}$ | + 9.3 | $1 \cdot 10^{-2.11}$ |
| $Pb^{2+}$ | +35.2 | $1 \cdot 10^{-1.24}$ |

As the above results indicate, the resulting electrode is primarily and preferentially selective to zinc ion $Zn^{+2}$ activity.

This invention comprises ion-selective electrodes for the analysis of concentration or activity of zinc ions in solution. The essence of the invention is the selection of solvents and ion-exchangers in the membrane. The membrane is fabricated by known methods either in the form of a polyvinylchloride or polyurethane membrane incorporating the solvent and the ion-exchanger or in the form of a liquid layer supported by a porous inert material like sintered glass or filters, the liquid consisting of the solvent and the ion-exchanger.

A wide range of solvents and ion-exchangers have been investigated, and it has been found that the suitable solvents have one of the following general formulas:

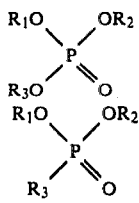

A  triesters of phosphoric acid

B  phosphonates ($R_3 \neq H$) or phosphinates ($R_3 = H$)

R denotes organic alkyl or aryl substituents like octylgroups, phenylgroups or octylphenylgroups. The solvent used in the experiments described in Example I and II is obtained if $R_1=R_2=R_3=$2-ethylhexyl-$=-C_8H_{17}$ in the structure A. The solvent should have a very low solubility in water and it is therefore advantageous to give the solvent hydrophobic character by choosing the substituents appropriately.

The ion-exchangers should have the following general formula:

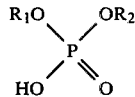

C  diesters or monoesters ($R_2 = H$) of phosphoric acid

R denotes a variety of organic substituents, e.g., ethylgroups, benzylgroups, phenylgroups, nitrophenylgroups, octylphenylgroups, octylbromophenylgroups and ethoxychains ($R'O(CH_2CH_2O)_nCH_2CH_2-$). The ion-exchanger used in Example II is obtained if $R_1=R_2=$2-ethylhexyl$--C_8H_{17}$ in the structure C. The ion-exchanger should also have a very low solubility in water, it should have a high acidity in order to give an electrode with low pH-dependence and it should be a strong complexing agent for preferably zinc ions. The rate of zinc ion exchange between the zinc-ligand complex in the membrane and zinc ions in the sample solution should also be high.

When one of the solvents mentioned is combined with one of the ion-exchangers mentioned, the following aspects should be considered. The solvent should be able to dissolve as much as possible of the zinc ion-exchanger complex, preferably more than 0.01 M. The zinc ion-exchanger content of the membrane in Example II was 0.13 M. The dissolution rate of solvent and ion-exchanger from the membrane into the aqueous sample solution should be as similar as possible in order to prevent changes in the membrane composition with time, which may result in drift of the electrode potential.

The selectivities of the composite membrane depends on both the solvent and ion-exchanger properties. The solvent may give selectivity for zinc over some interfering ions and the ion-exchanger may give selectivity for zinc over some other interfering ions. The combination should preferably give selectivity for zinc over all potential interefering ions.

The following data give the selectivity coefficients, expressed as $pK_{ZnM}=-\log K_{ZnM}$, for zinc over some interfering ions for a number of solvents, S.

| Cation | S1 | S2 | $pK_{ZnM}$ S3 | S4 | S5 |
|---|---|---|---|---|---|
| Li$^+$ | −2.60 | −2.38 | −2.54 | −0.20 | 0.28 |
| Na$^+$ | −1.18 | −0.81 | −0.58 | +1.22 | +1.45 |
| K$^+$ | −0.65 | −0.19 | −0.42 | +2.45 | +2.56 |
| Rb$^+$ | −0.55 | −0.11 | +0.69 | +2.88 | +3.02 |
| Cs$^+$ | −0.44 | +0.01 | −0.84 | +2.88 | +3.02 |
| Mg$^{2+}$ | −0.01 | −0.02 | +0.60 | +3.42 | +4.27 |
| Ca$^{2+}$ | −0.38 | −0.70 | −1.54 | +2.19 | +2.83 |
| Sr$^{2+}$ | −0.25 | +0.21 | −0.45 | +3.37 | +4.70 |
| Ba$^{2+}$ | −0.38 | +0.37 | −0.92 | +3.48 | +4.64 |
| Cu$^{2+}$ | −0.79 | −0.79 | −0.10 | +1.71 | +1.91 |
| Zn$^{2+}$ | 0 | 0 | 0 | 0 | 0 |
| Cd$^{2+}$ | −1.03 | −0.97 | −0.50 | +1.70 | +2.13 |
| Pb$^{2+}$ | −1.33 | −1.37 | −1.18 | +0.95 | +1.32 | where:
S1 = di-n-butylbutylphosphonate
S2 = di-n-amylamylphosphonate
S3 = di-n-octylphenylphosphonate
S4 = tri-n-octylphosphate
S5 = tri-2-ethylhexylphosphate The following data give the selectivity coefficients, expressed as $pK_{ZnM}=-\log K_{ZnM}$, for zinc over some interfering ions for a number of ion-exchangers in the solvent tri-2-ethylhexylphosphate ($=S5$).

| Cation | L1 | L2 | L3 | L4 | L5 | L6 | L7 | L8 | L9 | L10 | L11 | L12 |
|---|---|---|---|---|---|---|---|---|---|---|---|---|
| Li$^+$ | −0.36 | −0.13 | −0.19 | −0.52 | −0.59 | 0.25 | +0.32 | +0.83 | −0.51 | +0.50 | −0.22 | −0.41 |
| Na$^+$ | +0.96 | +0.66 | +0.82 | +1.11 | −1.05 | +1.07 | +1.94 | +2.31 | −1.55 | +1.49 | +1.09 | +0.15 |
| K$^+$ | +1.66 | +1.92 | +2.42 | +2.19 | +2.13 | +2.62 | +2.99 | +2.97 | −1.49 | +1.26 | +1.52 | −0.28 |
| Rb$^+$ | +1.75 | +2.06 | +2.67 | +2.24 | +2.17 | +2.91 | +2.99 | +2.84 | −1.54 | +1.42 | +1.54 | −0.11 |
| Cs$^+$ | +1.56 | +2.12 | +2.74 | +2.30 | +2.24 | +3.10 | +2.99 | +1.96 | −1.11 | +1.28 | +1.26 | +0.27 |
| Mg$^{2+}$ | +2.86 | +3.41 | +3.87 | +2.79 | +2.73 | +3.68 | +3.55 | +0.94 | +1.46 | +2.01 | +0.21 | +0.64 |
| Ca$^{2+}$ | +1.99 | +2.42 | +2.82 | +1.59 | −1.53 | +2.25 | −1.88 | −0.79 | −0.15 | −0.33 | −1.87 | −0.31 |
| Sr$^{2+}$ | +2.88 | +3.41 | +4.10 | +2.74 | +2.69 | +3.74 | +3.56 | +0.52 | +1.48 | +1.87 | +0.18 | −0.05 |
| Ba$^{2+}$ | +2.85 | +3.16 | +3.71 | +2.81 | +2.74 | +3.82 | +3.77 | +1.42 | +0.68 | +1.42 | +0.80 | −0.01 |
| Cu$^{2+}$ | +1.79 | +1.91 | +1.81 | +1.62 | −1.54 | +1.95 | +1.89 | +1.05 | −0.01 | +0.23 | −1.16 | −0.34 |
| Zn$^{2+}$ | 0 | 0 | 0 | 0 | 0 | 0 | 0 | 0 | 0 | 0 | 0 | 0 |
| Cd$^{2+}$ | +1.78 | +2.11 | +2.05 | +1.60 | −1.54 | +2.22 | −2.11 | −0.86 | −0.09 | +0.25 | −1.11 | −0.39 |
| Pb$^{2+}$ | +1.53 | +1.53 | −1.60 | +0.89 | −0.82 | −1.54 | −1.24 | −0.13 | −1.53 | −1.69 | −2.78 | −1.37 | where:
L1 = dimethylphosphoric acid
L2 = diethylphosphoric acid
L3 = di-iso-amylphosphoric acid
L4 = diphenylphosphoric acid
L5 = di-4-nitrophenylphosphoric acid
L6 = dibenzylphosphoric acid
L7 = di-2-ethylhexylphosphoric acid
L8 = di-octylphenylphosphoric acid
L9–L12 = organic phosphate esters; general formula $(RO(CH_2CH_2O)_n)_2PO_2H$.

The data thus relates to a combination between a certain solvent and various ligands as it is not possible to measure the ligand selectivity separately. The selectivity of the ligand itself can be computed as a difference between the selectivity of the composite membrane and the solvent selectivity. If the ligand selectivities are computed from measurements in two different solvents, the following results are obtained:

| Cation | $pK_{ZnM}$(composite membrane) $-pK_{ZnM}$(solvent) | | | |
|---|---|---|---|---|
| | L7 | | L8 | |
| for in | S3 | S5 | S3 | S5 |
| $Li^+$ | +0.85 | +0.60 | +2.29 | +1.11 |
| $Na^+$ | +0.85 | +0.49 | +2.02 | +0.86 |
| $K^+$ | +0.88 | +0.43 | +1.56 | +0.41 |
| $Rb^+$ | +0.82 | −0.03 | +1.35 | −0.18 |
| $Cs^+$ | +0.77 | −0.03 | +1.14 | −1.06 |
| $Mg^{2+}$ | −0.23 | −0.72 | −0.53 | −3.33 |
| $Ca^{2+}$ | −1.23 | −0.95 | −2.35 | −3.62 |
| $Sr^{2+}$ | −0.50 | −1.14 | −2.66 | −4.18 |
| $Ba^{2+}$ | −0.04 | −0.87 | −0.21 | −3.22 |
| $Cu^{2+}$ | 0.35 | −0.02 | +0.19 | −0.86 |
| $Zn^{2+}$ | 0 | 0 | 0 | 0 |
| $Cd^{2+}$ | −0.48 | −0.02 | +0.03 | −1.27 |
| $Pb^{2+}$ | −0.69 | −0.08 | −0.58 | −1.45 |

The ligand selectivities obtained by this method are useful when choosing a properly combined membrane. Depending on the intended application, it may be advantageous to make the selection so that the selectivity for zinc over a particular interfering ion is enhanced. For medical applications, selectivities over sodium, potassium and calcium will be important while selectivities over lithium, strontium or barium are of less importance.

Since various changes may be made in the above method without departing from the scope of the present invention, it is intended that all matter contained in the above description or shown in the accompanying drawings and claims shall be interpreted in an illustrative and not in a limiting sense.

What is claimed is:

1. An electrode preferentially sensitive to the activity of zinc ions, $Zn^{+2}$, in solution comprising:

a liquid organic phase containing (a) a liquid ion-exchanger selected from the group consisting of di-2-ethylhexylphosphoric acid and di-octylphenylphosphoric acid, dissolved in (b) tri-2-ethylhexylphosphate;

means for so containing the liquid organic phase as to provide an interface for ion exchange between said organic phase and the solution; and means for forming an electrical contact with said liquid organic phase at a fixed contact potential.

2. Method of preferentially measuring the activity of zinc ions, $Zn^{+2}$, in solution comprising the steps of:

establishing a stable electrical contact potential with a portion of a unitary body of substantially water-insoluble liquid organic phase containing (a) a liquid ion-exchanger selected from the group consisting of di-2-ethylhexylphosphoric acid and di-octylphenylphosphoric acid, dissolved in (b) tri-2-ethylhexylphosphate;

contacting another portion of said body with said solution; and detecting the potential arising across the interface between said body and said solution.

3. An electrode preferentially sensitive to the activity of zinc ions, $Zn^{+2}$, in solution comprising:

a liquid organic phase containing (a) a liquid ion-exchanger selected from the group consisting of di-2-ethylhexylphosphoric acid and di-octylphenylphosphoric acid, dissolved in (b) tri-n-octylphosphate;

means for so containing the liquid organic phase as to provide an interface for ion exchange between said organic phase and the solution; and means for forming an electrical contact with said liquid organic phase at a fixed contact potential.

4. Method of preferentially measuring the activity of zinc ions, $Zn^{+2}$, in solution comprising the steps of:

establishing a stable electrical contact potential with a portion of a unitary body of substantially water-insoluble liquid organic phase containing (a) a liquid ion-exchanger selected from the group consisting of di-2-ethylhexylphosphoric acid and di-octylphenylphosphoric acid, dissolved in (b) tri-n-octylphosphate;

contacting another portion of said body with said solution; and detecting the potential arising across the interface between said body and said solution.

* * * * *